(12) United States Patent
Gengler et al.

(10) Patent No.: US 9,078,438 B2
(45) Date of Patent: Jul. 14, 2015

(54) HAND WASH COMPOSITIONS

(75) Inventors: Arnoud U. M. Gengler, De Wijk (NL);
Meredith O. Theelen, Utrecht (NL);
Ragna M. S. van den Heuvel, Maarssen (NL)

(73) Assignee: Diversey, Inc., Sturtevant, WI (US)

( * ) Notice: Subject to any disclaimer, the term of this patent is extended or adjusted under 35 U.S.C. 154(b) by 0 days.

(21) Appl. No.: 14/233,852

(22) PCT Filed: Jul. 20, 2012

(86) PCT No.: PCT/US2012/047636
§ 371 (c)(1),
(2), (4) Date: Jan. 20, 2014

(87) PCT Pub. No.: WO2013/013164
PCT Pub. Date: Jan. 24, 2013

(65) Prior Publication Data
US 2014/0155454 A1    Jun. 5, 2014

Related U.S. Application Data

(60) Provisional application No. 61/509,723, filed on Jul. 20, 2011.

(51) Int. Cl.
| C11D 1/29 | (2006.01) |
| A01N 37/46 | (2006.01) |
| A01N 43/38 | (2006.01) |
| A61K 8/49 | (2006.01) |
| A61Q 17/00 | (2006.01) |
| A61Q 19/10 | (2006.01) |
| C11D 1/14 | (2006.01) |
| C11D 3/39 | (2006.01) |
| C11D 3/48 | (2006.01) |

(52) U.S. Cl.
CPC .............. *A01N 43/38* (2013.01); *A01N 37/46* (2013.01); *A61K 8/492* (2013.01); *A61K 8/4913* (2013.01); *A61Q 17/005* (2013.01); *A61Q 19/10* (2013.01); *C11D 1/146* (2013.01); *C11D 1/29* (2013.01); *C11D 3/3947* (2013.01); *C11D 3/48* (2013.01)

(58) Field of Classification Search
None
See application file for complete search history.

(56) References Cited

U.S. PATENT DOCUMENTS 5,616,335 A    4/1997    Nicolle et al.

FOREIGN PATENT DOCUMENTS

| EP | 0890635 | | 1/1999 |
| EP | 0890635 A2 | * | 1/1999 |
| EP | 1780260 | | 5/2007 |
| EP | 1780260 A1 | * | 5/2007 |
| WO | 2004/110610 | | 12/2004 |
| WO | 2005/100529 | | 10/2005 |
| WO | 2010/078883 | | 7/2010 |

OTHER PUBLICATIONS

International Search Report, PCT/US2012/047636, dated Jul. 20, 2012.

* cited by examiner

*Primary Examiner* — Anand Desai
*Assistant Examiner* — Melissa Mercier
(74) *Attorney, Agent, or Firm* — Michael Best & Friedrich LLP (57) ABSTRACT

Hand wash compositions including ε-phthalimido-peroxyhexanoic acid are described herein.

26 Claims, 2 Drawing Sheets

Table 1. Exemplary formulations.

| Composition | Sunflower Oil | NaOH (50%) | PAP | Salicylic acid | Citric acid | Soft care mild | water | pH |
|---|---|---|---|---|---|---|---|---|
| 1 | - | 0.4 | - | 1 | 0.4 | - | 98.2 | 4 |
| 2 | - | 0.4 | 0.3 | 1 | 0.4 | - | 98.9 | 4 |
| 3 | - | 0.4 | 0.3 | 1 | 1.25 | - | 58.05 | 3.5 |
| 4 | - | 0.5 | 0.5 | 1 | 0.5 | - | 97.5 | 3.5 |
| 5 | - | 0.4 | 0.5 | - | 1.25 | - | 57.65 | 3.5 |
| 6 | - | 0.6 | 1 | 1 | 1.25 | - | 96.15 | 3.7 |
| 7 | - | 0.4 | 1 | - | 1.25 | - | 57.35 | 3.5 |
| 8 | - | 0.4 | 1.5 | 1 | 0.5 | - | 97.1 | 3.7 |
| 9 | - | 0.4 | 1.5 | - | 1.25 | - | 96.1 | 3.5 |
| 10 | 22.5 | 0.5 | 3 | 0.5 | 1 | - | 72.5 | 3.5 |
| 11 | - | 0.5 | 0.5 | 1 | 0.5 | - | 97.5 | 3.5 |
| 12 | - | 0.4 | 0.5 | - | 1.25 | - | 97.65 | 3.5 |
| 13 | - | 0.6 | 1 | 1 | 1.25 | - | 96.15 | 3.7 |
| 14 | - | 0.4 | 1 | - | 1.25 | - | 97.35 | 3.5 |
| 15 | - | - | 0.5 | 1 | 0.6 | 97.7 | - | 3.6 |
| 16 | - | - | 0.5 | - | 1.34 | 96.16 | - | 3.6 |
| 17 | - | - | 1 | 1 | 0.6 | 97.2 | - | 3.7 |
| 18 | - | - | 1 | - | 1.34 | 97.66 | - | 3.6 |
| 19 | 22.5 | 0.5 | 3 | 1 | 1 | - | 72 | 3.5 |
| 20 | 17.5 | 0.5 | 3 | 0.5 | 1 | - | 77.5 | 3.5 |
| 21 | - | - | 0.1 | 1.5 | - | 98.4 | - | 5.5 |
| 22 | - | - | 0.1 | 2 | - | 97.9 | - | 5.5 |
| 23 | - | - | 0.1 | 2.5 | - | 97.4 | - | 5.5 |
| 24 | - | - | - | 1.5 | 1 | 97.5 | - | 4 |
| 25 | - | - | - | 2 | 1 | 97 | - | 4 |
| 26 | - | - | - | 2.5 | 1 | 96.5 | - | 4 |
| 27 | - | - | - | 2 | 0.1 | 97.9 | - | 4 |
| 28 | - | - | 0.2 | 2 | - | 97.8 | - | 5 |
| 29 | - | - | 0.35 | 2 | - | 97.65 | - | 6 |
| 30 | - | - | 0.6 | 2 | - | 97.4 | - | 7 |
| 31 | - | - | - | 1.5 | 1 | 0.1 | 95.9 | 3.5 |
| 32 | - | - | - | 2 | 1 | 0.1 | 96.9 | 3.5 |
| 33 | - | - | - | 2.5 | 1 | 0.1 | 96.4 | 3.5 |
| 34 | - | - | - | 1.5 | - | 0.3 | 98.2 | 3.5 |
| 35 | - | - | - | 2 | - | 0.3 | 97.7 | 3.5 |
| 36 | - | - | - | 2.5 | - | 0.3 | 97.2 | 3.5 |
| 37 | - | - | - | 3 | 1 | 0.1 | 95.9 | 3.5 |
| 38 | - | - | - | 3 | - | 0.3 | 96.7 | 3.5 |
| 39 | - | - | - | 3.5 | 1 | 0.1 | 95.4 | 3.5 |
| 40 | - | - | - | 3.5 | - | 0.3 | 96.2 | 3.5 |

Table 1. Exemplary formulations.

| Composition | Sunflower Oil | NaOH (50%) | PAP | Salicylic acid | Citric acid | Soft care mild | water | pH |
|---|---|---|---|---|---|---|---|---|
| 1 | - | 0.4 | - | 1 | 0.4 | - | 98.2 | 4 |
| 2 | - | 0.4 | 0.3 | 1 | 0.4 | - | 98.9 | 4 |
| 3 | - | 0.4 | 0.3 | - | 1.25 | - | 98.05 | 3.5 |
| 4 | - | 0.5 | 0.5 | 1 | 0.5 | - | 97.5 | 3.5 |
| 5 | - | 0.4 | 0.5 | - | 1.25 | - | 97.85 | 3.5 |
| 6 | - | 0.6 | 1 | 1 | 1.25 | - | 96.15 | 3.7 |
| 7 | - | 0.4 | 1 | - | 1.25 | - | 97.35 | 3.5 |
| 8 | - | 0.4 | 1.5 | 1 | 0.5 | - | 97.1 | 3.7 |
| 9 | - | 0.4 | 1.5 | - | 1.25 | - | 98.1 | 3.5 |
| 10 | 22.5 | 0.5 | 3 | 0.5 | 1 | - | 72.5 | 3.5 |
| 11 | - | 0.5 | 0.5 | 1 | 0.5 | - | 97.5 | 3.5 |
| 12 | - | 0.4 | 0.5 | - | 1.25 | - | 97.85 | 3.5 |
| 13 | - | 0.6 | 1 | 1 | 1.25 | - | 96.15 | 3.7 |
| 14 | - | 0.4 | 1 | - | 1.25 | - | 97.35 | 3.5 |
| 15 | - | - | 0.5 | 1 | 0.9 | 97.7 | - | 3.6 |
| 16 | - | - | 0.5 | - | 1.34 | 98.16 | - | 3.6 |
| 17 | - | - | 1 | 1 | 0.9 | 97.2 | - | 3.7 |
| 18 | - | - | 1 | - | 1.34 | 97.66 | - | 3.6 |
| 19 | 22.5 | 0.5 | 3 | 1 | 1 | - | 72 | 3.5 |
| 20 | 17.5 | 0.5 | 3 | 0.5 | 1 | - | 77.5 | 3.5 |
| 21 | - | 0.1 | 1.5 | - | - | 98.4 | - | 5.5 |
| 22 | - | 0.1 | 2 | - | - | 97.9 | - | 5.5 |
| 23 | - | 0.1 | 2.5 | - | - | 97.4 | - | 5.5 |
| 24 | - | - | 1.5 | 1 | - | 97.5 | - | 4 |
| 25 | - | - | 2 | 1 | - | 97 | - | 4 |
| 26 | - | - | 2.5 | 1 | - | 96.5 | - | 4 |
| 27 | - | - | 2 | - | 0.1 | 97.9 | - | 4 |
| 28 | - | 0.2 | 2 | - | - | 97.8 | - | 5 |
| 29 | - | 0.35 | 2 | - | - | 97.65 | - | 6 |
| 30 | - | 0.6 | 2 | - | - | 97.4 | - | 7 |
| 31 | - | - | 1.5 | 1 | 0.1 | 96.9 | - | 3.5 |
| 32 | - | - | 2 | 1 | 0.1 | 96.9 | - | 3.5 |
| 33 | - | - | 2.5 | 1 | 0.1 | 96.4 | - | 3.5 |
| 34 | - | - | 1.5 | - | 0.3 | 98.2 | - | 3.5 |
| 35 | - | - | 2 | - | 0.3 | 97.7 | - | 3.5 |
| 36 | - | - | 2.5 | - | 0.3 | 97.2 | - | 3.5 |
| 37 | - | - | 3 | 1 | 0.1 | 95.9 | - | 3.5 |
| 38 | - | - | 3 | - | 0.3 | 96.7 | - | 3.5 |
| 39 | - | - | 3.5 | 1 | 0.1 | 95.4 | - | 3.5 |
| 40 | - | - | 3.5 | - | 0.3 | 96.2 | - | 3.5 |

FIGURE 1

Table 2. Antimicrobial activities of exemplary formulations.

| Composition | Contact time [sec] | Temp [oC] | P. aeruginosa ATCC15442 | | | | S. aureus ATCC 6538 | | | |
|---|---|---|---|---|---|---|---|---|---|---|
| | | | Clean conditions | | Dirty conditions | | Clean conditions | | Dirty conditions | |
| | | | 50% | 80% | 50% | 80% | 50% | 80% | 50% | 80% |
| 1 | 60 | 20 | <4,1 | >5,6 | <4,1 | <4,1 | >5,6 | <4,1 | <4,1 | <4,1 |
| 2 | 60 | 20 | <4,1 | >5,6 | >5,6 | <4,1 | >5,6 | >5,6 | >5,6 | >5,6 |
| 3 | 60 | 20 | >5,6 | >5,6 | <5,6 | 4.5 | >5,6 | >5,6 | 5.2 | >5,6 |
| 4 | 60 | 20 | >5,6 | >5,6 | >5,6 | >5,6 | >5,6 | >5,6 | >5,6 | >5,6 |
| 5 | 60 | 20 | >5,6 | >5,6 | >5,6 | >5,6 | >5,6 | >5,6 | >5,6 | >5,6 |
| 6 | 60 | 20 | >5,6 | >5,6 | >5,6 | >5,6 | >5,6 | >5,6 | >5,6 | >5,6 |
| 7 | 60 | 20 | >5,6 | >5,6 | >5,6 | >5,6 | >5,6 | >5,6 | >5,6 | >5,6 |
| 8 | 60 | 20 | >5,6 | >5,6 | >5,6 | >5,6 | >5,6 | >5,6 | >5,6 | >5,6 |
| 9 | 60 | 20 | >5,6 | >5,6 | >5,6 | >5,6 | >5,6 | >5,6 | >5,6 | >5,6 |
| 10 | 60 | 20 | >5,6 | >5,6 | <4,2 | >5,6 | >5,6 | >5,6 | >5,6 | >5,6 |
| 11 | 30 | 20 | >5 | >5 | <4,1 | >5 | >5 | >5 | >5 | >5 |
| 12 | 30 | 20 | 4.4 | >5 | <4,1 | >5 | >5 | >5 | >5 | >5 |
| 13 | 30 | 20 | >5 | >5 | >5 | >5 | >5 | >5 | >5 | >5 |
| 14 | 30 | 20 | >5 | >5 | 5.4 | >5 | >5 | >5 | >5 | >5 |
| 15 | 30 | 20 | >5 | >5 | 5.4 | >5 | >5 | >5 | <4,3 | <4,3 |
| 16 | 30 | 20 | <4,1 | >5 | <4,1 | <4,1 | <4,3 | <4,3 | <4,3 | <4,3 |
| 17 | 30 | 20 | >5 | >5 | <4,1 | >5 | >5 | >5 | <4,3 | 4.5 |
| 18 | 30 | 20 | <4,1 | >5 | <4,1 | 5.3 | <4,3 | <4,3 | <4,3 | <4,3 |
| 19 | 60 | 20 | >5 | >5 | 5.4 | >5 | >5 | >5 | >5 | >5 |
| 20 | 60 | 20 | >5 | >5 | >5 | >5 | >5 | >5 | >5 | >5 |
| 21 | 30 | 20 | <4,2 | <4,2 | <4,2 | <4,2 | <4,1 | <4,1 | <4,1 | <4,1 |
| 22 | 30 | 20 | <4,2 | <4,2 | <4,2 | <4,2 | <4,1 | <4,1 | <4,1 | <4,1 |
| 23 | 30 | 20 | <4,2 | <4,2 | <4,2 | <4,2 | <4,1 | <4,1 | <4,1 | <4,1 |
| 24 | 30 | 20 | >5 | >5 | >5 | 4.2 | 5.4 | 4.5 | <4,1 | <4,1 |
| 25 | 30 | 20 | >5 | >5 | <4,2 | <4,1 | 4.9 | <4,1 | >5 | <4,1 |
| 26 | 30 | 20 | 5.3 | >5 | <4,2 | >5 | 3.5 | <4,1 | <4,1 | <4,1 |
| 27 | 30 | 20 | <4,2 | <4,2 | <4,2 | <4,2 | <4,1 | <4,1 | <4,1 | <4,1 |
| 28 | 30 | 20 | <4,2 | <4,2 | <4,2 | <4,2 | <4,1 | <4,1 | <4,1 | <4,1 |
| 29 | 30 | 20 | <4,2 | <4,2 | <4,2 | <4,2 | <4,1 | <4,1 | <4,1 | <4,1 |
| 30 | 30 | 20 | <4,2 | <4,2 | <4,2 | <4,2 | <4,1 | <4,1 | <4,1 | <4,1 |
| 31 | 30 | 20 | >5 | >5 | >5 | >5 | >5 | >5 | 4.2 | 4.2 |
| 32 | 30 | 20 | >5 | >5 | 5.6 | >5 | >5 | >5 | 4.8 | >5 |
| 33 | 30 | 20 | >5 | >5 | >5 | >5 | <3,9 | >5 | >5 | >5 |
| 34 | 30 | 20 | 4.9 | >5 | 5.2 | >5 | <3,9 | <3,9 | <3,9 | <3,9 |
| 35 | 30 | 20 | 5.1 | >5 | <4,2 | >5 | <3,9 | <3,9 | <3,9 | <3,9 |
| 36 | 30 | 20 | >5 | >5 | <4,1 | >5 | >5 | >5 | <3,9 | <3,9 |
| 37 | 30 | 20 | >5 | >5 | >5 | >5 | >5 | >5 | >5 | >5 |
| 38 | 30 | 20 | >5 | >5 | >5 | >5 | >5 | >5 | >5 | >5 |
| 39 | 30 | 20 | >5 | >5 | >5 | >5 | >5 | >5 | >5 | >5 |
| 40 | 30 | 20 | >5 | >5 | >5 | >5 | >5 | >5 | >5 | >5 |

FIGURE 2

HAND WASH COMPOSITIONS

CROSS-REFERENCE TO RELATED APPLICATIONS

This patent application is a national stage filing under 35 U.S.C. 371 of International Application No. PCT/US2012/047636, filed on Jul. 20, 2012, which claims the benefit of priority to U.S. Provisional Application No. 61/509,723, filed on Jul. 20, 2011, the disclosures of which are incorporated by reference herein in their entireties. Priority to each application is hereby claimed.

BACKGROUND

Hand washing is an important part of a hygiene program for health care workers and food handlers, who may wash their hands many times a day. Many currently available cleansing products used in these settings include active antimicrobial ingredients that may irritate the skin with regular, frequent, and/or repeated use, which may lead to poor compliance by the personnel who have mandatory hand wash guidelines. Other hand washes include active ingredients that may have a limited spectrum of antimicrobial activity, or may present safety or environmental concerns.

SUMMARY

In one aspect, the disclosure provides a hand wash composition comprising from about 0.3 wt % to about 8.0 wt % $\epsilon$-phthalimido-peroxyhexanoic acid, and at least one anionic surfactant, wherein the composition has a maximum inorganic salt concentration of 0.2 wt % and a pH of from about 2.5 to about 4.5.

In another aspect, the disclosure provides a method of disinfecting the skin, comprising contacting the skin with a composition comprising from about 0.3 wt % to about 8.0 wt % $\epsilon$-phthalimido-peroxyhexanoic acid.

Other aspects and embodiments are encompassed by the disclosure and will become apparent in light of the following description and drawings

BRIEF DESCRIPTION OF THE DRAWINGS

FIG. 2 depicts a table (Table 2) of data illustrating the antimicrobial activity of non-limiting embodiments of compositions described herein.

DETAILED DESCRIPTION

The disclosure provides a stable hand wash composition that may be highly effective in killing bacteria and other microorganisms, with a safe and effective active ingredient, and yet be mild enough for frequent use. Such compositions may be useful in the healthcare and patient care industries, for example as a hand wash or a surgical scrub, as well as in the food and beverage industry. The hand wash compositions include $\epsilon$-phthalimido-peroxyhexanoic acid (PAP). The compositions may feature high antimicrobial activity at short contact times, may have good stability, and may be mild enough to allow for repeated hand washing without irritating the skin.

DEFINITIONS

As used herein, "by weight" refers to the total weight of the composition. For example, if a composition has a total weight of 100 grams and comprises 40% (by weight) of a surfactant, the composition comprises 40 grams of surfactant. As will be recognized by those skilled in the art, some commercially available components, such as surfactants, thickeners and other composition components, are sold as solutions; e.g., a certain percentage of the component in a solution such as water. If such a solution is used to formulate a composition, it is to be understood that the percent by weight of the component given herein is referring to the percent by weight of the solution containing the component.

The term "antimicrobial," when used in the context of an antimicrobial agent or antimicrobial composition, refers to an agent or composition that can kill or otherwise inhibit the growth or proliferation of microbes including, for example, bacteria, viruses and fungi. Similarly, the term "antimicrobial activity" as used herein refers to activity that can kill or otherwise inhibit the growth or proliferation of microbes including bacteria, yeasts, viruses and fungi.

The term "cleansing", as used herein, refers to washing, cleaning, or otherwise removing unwanted material, e.g., from the skin.

The term "disinfecting", as used herein, refers broadly to deactivating, inhibiting, disabling, killing, or otherwise sterilizing a microorganism including, for example, bacteria, yeast, viruses and fungi. In embodiments, disinfecting involves $\geq 3$ log reduction in microorganisms, e.g., $\geq 4$ log reduction or $\geq 5$ log reduction.

The term "stable" or "stability", as used herein, refers to physical and/or chemical stability. Physical stability refers to retaining an original physical form without undergoing phase change or separation, discoloration, and the like. Chemical stability refers to resistance to impurity generation and degradation of active components.

The hand wash compositions described herein may comprise, consist of or consist essentially of the indicated components. The term "consisting essentially of" shall be construed to mean that a composition includes the listed components and optionally additional components that do not materially affect the basic and novel properties of the composition. As used herein, the "basic and novel property" of a composition is its antimicrobial activity. Routine experiments, such as those described herein, may be performed to determine whether there is a material effect or not. In some embodiments, a composition consisting essentially of indicated components may not include additional components that enhance antimicrobial activity, such as, for example, hydrogen peroxide.

The term "inorganic salt" as used herein refers to salts that do not contain carbon, that result from replacement of one or more hydrogens of an inorganic acid with one or more metal ions. The metal ion may be an alkali, alkaline earth or transition metal ion. The anion of the inorganic salt may be a monovalent anion, including but not limited to halides (e.g., chloride), or a polyvalent anion including but not limited to sulfate, phosphate, nitrate, borate, and the like. Such inorganic salts may be added directly to the compositions or may form in the compositions as a result of addition of certain components. For example, addition of hydrochloric acid and sodium hydroxide may result in sodium chloride formation. The term "inorganic salt" is not intended to encompass salts of surfactants,

It is specifically understood that any numerical value recited herein (e.g., ranges) includes all values from the lower value to the upper value, i.e., all possible combinations of numerical values between the lowest value and the highest value enumerated are to be considered to be expressly stated in this application. For example, if a concentration range is stated as 1% to 50%, it is intended that values such as 2% to 40%, 10% to 30%, or 1% to 3%, etc., are expressly enumerated in this specification. These are only examples of what is specifically intended.

Compositions

PAP

The hand wash compositions disclosed herein include ε-phthalimido-peroxyhexanoic acid (PAP). As used herein, ε-phthalimido-peroxyhexanoic acid or PAP refer to the compound with CAS Number 128275-31-0, as illustrated below and which is also referred to by other synonyms such as 6-phthalimidoperoxyhexanoic acid, phthalimidoperoxycaproic acid, 6-phthalimido hexaneperoxoic acid, ε-phthaloylaminoperoxycaproic acid, 3-dihydro-1,3-dioxo-2H-isoindole-2-hexaneperoxoic acid, and the like.

PAP

PAP is known to have disinfecting properties and has been used, for example, in toothpaste and in fabric care products. In the compositions described herein (e.g., personal care compositions such as hand washes), PAP is stable at concentrations that provide high disinfectant activities at suitably short contact times. The compositions described herein can include PAP at concentrations of about 0.3 wt % to about 8.0 wt %, for example about 3.0 wt % to about 5.0 wt %, or about 3.5 wt % to about 4.5 wt %, or about 4.0 wt %. In embodiments, the compositions can include at least about 0.3 wt %, at least about 0.5 wt %, at least about 0.7 wt %, at least about 0.8 wt %, at least about 0.9 wt %, at least about 1.0 wt %, at least about 1.5 wt %, at least about 2.0 wt %, at least about 2.5 wt %, at least about 3.0 wt %, at least about 3.5 wt %, at least about 4.0 wt %, at least about 4.5 wt %, at least about 5.0 wt %, at least about 5.5 wt %, at least about 6.0 wt %, at least about 6.5 wt %, at least about 7.0 wt %, at least about 7.5 wt %, at least about 8.0 wt %, up to about 0.3 wt %, 0.5 wt %, up to about 0.7 wt %, up to about 0.8 wt %, up to about 0.9 wt %, up to about 1.0 wt %, up to about 1.5 wt %, up to about 2.0 wt %, up to about 2.5 wt %, up to about 3.0 wt %, up to about 3.5 wt %, up to about 4.0 wt %, up to about 4.5 wt %, up to about 5.0 wt %, up to about 5.5 wt %, up to about 6.0 wt %, up to about 6.5 wt %, up to about 7.0 wt %, up to about 7.5 wt %, or up to about 8.0 wt % PAP. In embodiments, the compositions comprise PAP at concentrations that are adequate for antimicrobial activity, and do not irritate the skin upon prolonged contact or frequent use.

The PAP included in the compositions and formulations described herein can be from any suitable source. For example, PAP is commercially available from suppliers such as Solvay Chemicals under the trademark EURECO™. For example, one form of PAP is EURECO HC L17, a liquid containing suspended particles of PAP. Alternatively, PAP can be produced using any synthetic route that is known in the art.

Surfactants

Suitable surfactants for use in the compositions include anionic surfactants, amphoteric surfactants, cationic surfactants, zwitterionic surfactants, non-ionic surfactants, and combinations thereof.

Suitable anionic surfactants include, for example, alkyl sulfates, alkyl ether sulfates, alkyl aryl sulfonates, alpha-olefin sulfonates, alkali metal or ammonium salts of alkyl sulfates, alkali metal or ammonium salts of alkyl ether sulfates, alkyl phosphates, silicone phosphates, alkyl glyceryl sulfonates, alkyl sulfosuccinates, alkyl taurates, acyl taurates, alkyl sarcosinates, acyl sarcosinates, sulfoacetates, alkyl phosphate esters, mono alkyl succinates, monoalkyl maleates, sulfoacetates, acyl isethionates, alkyl carboxylates, phosphate esters, sulfosuccinates (e.g., sodium dioctylsulfosuccinate), and combinations thereof. Some non-limiting examples of anionic surfactants include sodium lauryl sulfate, sodium lauryl ether sulfate, ammonium lauryl sulfosuccinate, ammonium lauryl sulfate, ammonium lauryl ether sulfate, sodium dodecylbenzene sulfonate, triethanolamine dodecylbenzene sulfonate, sodium cocoyl isethionate, sodium lauroyl isethionate, sodium N-lauryl sarcosinate, and combinations thereof.

Suitable cationic surfactants include, for example, alkyl ammonium salts, polymeric ammonium salts, alkyl pyridinium salts, aryl ammonium salts, alkyl aryl ammonium salts, silicone quaternary ammonium compounds, and combinations thereof. Some non-limiting examples of cationic surfactants include behenyltrimonium chloride, stearlkonium chloride, distearalkonium chloride, chlorohexidine digluconate, polyhexamethylene biguanide (PHMB), cetyl pyridinium chloride, benzammonium chloride, benzalkonium chloride, and combinations thereof.

Suitable amphoteric surfactants include, for example, betaines, alkylamido betaines, sulfobetaines, N-alkyl betaines, sultaines, amphoacetates, amophodiacetates, imidazoline carboxylates, sarcosinates, acylamphoglycinates, such as cocamphocarboxyglycinates and acylamphopropionates, and combinations thereof. Some non-limiting examples of amphoteric surfactants include cocamidopropyl betaine, lauramidopropyl betaine, meadowfoamamidopropyl betaine, sodium cocoyl sarcosinate, sodium cocamphoacetate, disodium cocoamphodiacetate, ammonium cocoyl sarcosinate, sodium cocoamphopropionate, and combinations thereof.

Suitable zwitterionic surfactants include, for example, alkyl amine oxides, silicone amine oxides, and combinations thereof. Some non-limiting examples of suitable zwitterionic surfactants include, for example, 4-[N,N-di(2-hydroxyethyl)-N-octadecylammonio]-butane-1-carboxylate, S—[S-3-hydroxypropyl-5-hexadecylsulfonio]-3-hydroxypentane-1-sulfate, 3-[P,P-diethyl-P-3,6,9-trioxatetradexopcylphosphonio]-2-hydroxypropane-1-phosphate, 3-[N,N-dipropyl-N-3-dodecoxy-2-hydroxypropylammonio]-propane-1-phosphonate, 3-(N,N-dimethyl-N-hexadecylammonio)propane-1-sulfonate, 3-(N,N-dimethyl-N-hexadecylammonio)-2-hydroxypropane-1-sulfonate, 4-[N,N-di(2-hydroxyethyl)-N-(2-hydroxydodecyl)ammonio]-butane-1-carboxylate, 3-[S-ethyl-S-(3-dodecoxy-2-hydroxypropyl)sulfonio]-propane-1-phosphate-, 3-[P,P-dimethyl-P-dodecylphosphonio]-propane-1-phosphonate, 5-[N,N-di(3-hydroxypropyl)-N-hexadecylammonio]-2-hydroxy-pentane-1-sulfate, and combinations thereof.

Suitable non-ionic surfactants include, for example, mono- and di-alkanolamides such as, for example, cocamide monoethanolamine and cocamide diethanolamine, amine oxides, alkyl polyglucosides, ethoxylated silicones, ethoxylated alcohols (e.g., ethoxylated lauryl alcohol, such as Laureth-4), ethoxylated carboxylic acids, ethoxylated fatty acids, ethoxylated amines, ethoxylated amides, ethoxylated alkylolamides, ethoxylated alkylphenols, ethoxylated glyceryl esters, ethoxylated sorbitan esters, ethoxylated phosphate esters, glycol stearate, glyceryl stearate, and combinations thereof.

Suitably, the compositions comprise at least one anionic surfactant, which may be present in an amount of about 1 to about 15 wt %. In embodiments, at least one anionic surfactant may be present in an amount of up to about 1 wt %, up to about 2 wt %, up to about 3 wt %, up to about 4 wt %, up to about 5 wt %, up to about 6 wt %, up to about 7 wt %, up to about 8 wt %, up to about 9 wt %, up to about 10 wt %, up to about 11 wt %, up to about 12 wt %, up to about 13 wt %, up to about 14 wt %, up to about 15 wt %, at least about 1 wt %, at least about 2 wt %, at least about 3 wt %, at least about 4 wt %, at least about 5 wt %, at least about 6 wt %, at least about 7 wt %, at least about 8 wt %, at least about 9 wt %, at least about 10 wt %, at least about 11 wt %, at least about 12 wt %, at least about 13 wt %, at least about 14 wt %, or at least about 15 wt %. Additional surfactants may also be present, for example, in amounts of up to about 1 wt %, up to about 2 wt %, up to about 3 wt %, up to about 4 wt %, up to about 5 wt %, up to about 6 wt %, up to about 7 wt %, up to about 8 wt %, up to about 9 wt %, up to about 10 wt %, up to about 11 wt %, up to about 12 wt %, up to about 13 wt %, up to about 14 wt %, up to about 15 wt %, at least about 1 wt %, at least about 2 wt %, at least about 3 wt %, at least about 4 wt %, at least about 5 wt %, at least about 6 wt %, at least about 7 wt %, at least about 8 wt %, at least about 9 wt %, at least about 10 wt %, at least about 11 wt %, at least about 12 wt %, at least about 13 wt %, at least about 14 wt %, or at least about 15 wt %. The compositions may include one surfactant or a combination of multiple surfactants of the same or different type as described above.

Thickeners

The compositions can comprise a thickening agent, which may act to thicken or increase the viscosity of the composition. A thickener may be added to form a viscous liquid, gel, or semisolid, which can be easily applied to and rubbed on the skin. Typically, a composition will comprise from about 0.05% to about 5% by weight of a thickening agent. In embodiments, a composition may include up to about 0.5 wt %, up to about 0.75 wt %, up to about 1.0 wt %, up to about 1.5 wt %, up to about 2.0 wt %, up to about 2.5 wt %, up to about 3.0 wt %, up to about 3.5 wt %, up to about 4.0 wt %, up to about 4.5 wt %, up to about 5.0 wt %, at least about 0.5 wt %, at least about 0.75 wt %, at least about 1.0 wt %, at least about 1.5 wt %, at least about 2.0 wt %, at least about 2.5 wt %, at least about 3.0 wt %, at least about 3.5 wt %, at least about 4.0 wt %, at least about 4.5 wt %, or at least about 5.0 wt % of a thickening agent.

Exemplary organic thickeners there include, but are not limited to, cellulosic thickeners and their derivatives, natural gums, crosslinked acrylates and sulfonates, starches, and fatty acid alcohols. Inorganic thickeners suitably comprise a salt or a clay. Some non-limiting examples of cellulosic thickeners include cellulose, methylcellulose, hydroxyethyl cellulose, hydroxypropyl cellulose, hydroxyethyl methylcellulose, hydroxypropyl methylcellulose, hydroxybutyl methylcellulose, carboxymethyl cellulose, carboxymethyl hydroxyethylcellulose, microcrystalline cellulose, sodium cellulose sulfate, and the like. Some non-limiting examples of natural gums include carrageenans, gelatin, agar, guar gum, hydroxypropyl guar, karaya gum, locust bean gum, tragacanth gum, xanthan gum, dehydroxanthan gum, gum arabic, gellan gum, pectin, amylopectin, furcellaran, sodium carrageenan, kelp, dextran, starch, modified starches, alginates such as propylene glycol alginate, chitosan, modified chitosans, silica, fumed silica, colloidal silica, and the like. Some non-limiting examples of acrylates include polyacrylic acid, sodium polyacrylate, sodium acrylate/vinyl alcohol copolymers, sodium polymethacrylate, acrylates/$C_{10}$-$C_{30}$ Alkyl Acrylate Crosspolymers, and the like, which may or may not be crosslinked. Commerically available polyacrylate polymers include those sold under the trade name Carbopol® (available from Lubrizol Corporation), such as Carbopol® 940 polymer or the Carbopol Ultrez series of polymers which include carbomers and acrylate/$C_{10}$-$C_{30}$ alkyl acrylate crosspolymers, Pemulen™ polymers (Lubrizol Corporation) which are crosslinked copolymers of acrylic acid and $C_{10}$-$C_{30}$ alkyl acrylate, and Structure® Plus (Akzo Nobel) which is an acrylate/aminoacrylate/$C_{10}$-$C_{30}$ alkyl PEG-20 itaconate copolymer. Some non-limiting examples of starches include flours and starches derived from any variety of plant sources such as, for example, oat flour, potato starch, wheat flour, wheat starch, and the like. Some non-limiting examples of fatty acid alcohols include caprylic alcohol, cetearyl alcohol, lauryl alcohol, oleyl alcohol, palm kernel alcohol, and the like. Some non-limiting examples of salts include calcium chloride, sodium chloride, sodium sulfate, magnesium sulfate, ammonium chloride, and the like. In embodiments in which inorganic salts are used as thickeners, care should be taken to avoid using amounts that may affect the stability of the composition (vide Some non-limiting examples of clays include bentonite, magnesium aluminum silicate, magnesium trisilicate, stearalkonium bentonite, tromethamine magnesium aluminum silicate, and the like.

The composition may comprise one thickener or a mixture of two or more thickeners. Suitably, a thickener is selected such that it will not adversely react with other materials in a composition. It is understood that a person skilled in the art will know how to select an appropriate thickener and control any adverse reactions through formulating.

Skin Conditioners

The compositions may include at least one skin conditioner such as an emollient, humectant, occlusive agent, or other moisturizer to provide moisturizing, skin softening, skin barrier maintenance, anti-irritation, or other skin health benefits. Some non-limiting examples of emollients include stearoxytrimethylsilane, alkyl benzoate, silicone oils, dimethicone, myristyl myristate, cetyl myristate, glyceryl dioleate, methyl laurate, PPG-9 laurate, octyl palmitate, lanolin, propylene glycol, glycerol, fatty acids, natural oils such as sunflower, almond, mineral, canola, sesame, soybean, wheat germ, corn, peanut and olive, isopropyl myristate, myristyl alcohol, aloe vera, hydrolyzed silk protein, Vitamin E, stearyl alcohol, isopropyl palmitate, sorbitol, amino acid complexes, and polyethylene glycol. Some non-limiting examples of humectants include hydroxyethyl urea, agarose, arginine PCA, fructose, glucose, glutamic acid, glycerol, honey, lactose, maltose, propylene glycol, polyethylene glycol, sorbitol and mixtures thereof. Some non-limiting examples of occlusive agents include petrolatum, shea butter, alkyl dimethicones, avocado oil, balm mint oil, canola oil, cod liver oil, corn oil, methicone, mineral oil, olive oil, phenyl trimethicone, trimyristin, soybean oil, glycol distearate, stearyl stearate, synthetic wax, or mixtures thereof. Some non-limiting examples of other moisturizers include cholesterol, cystine, hyaluronic acid, keratin, lecithin, egg yolk, glycine, PPG-12, panthenol, retinol, vegetable oil, and mixtures thereof. Some non-limiting examples of anti-irritants include bisabolol and panthenol.

The composition may include one skin conditioner or a mixture of more than one skin conditioner. Compositions may include from about 0.01 to about 10 wt % of a skin conditioner, e.g., from about 0.1 to about 5.0 wt %. In embodiments, a composition may include up to about 0.5 wt %, up to about 0.75 wt %, up to about 1.0 wt %, up to about 1.5 wt %, up to about 2.0 wt %, up to about 2.5 wt %, up to about 3.0 wt %, up to about 3.5 wt %, up to about 4.0 wt %, up to about 4.5 wt %, up to about 5.0 wt %, at least about 0.5 wt %, at least about 0.75 wt %, at least about 1.0 wt %, at least about 1.5 wt %, at least about 2.0 wt %, at least about 2.5 wt %, at least about 3.0 wt %, at least about 3.5 wt %, at least about 4.0 wt %, at least about 4.5 wt %, or at least about 5.0 wt % of a skin conditioner. For example, a composition may include from about 0.01 wt % to about 2.0 wt % of at least one emollient.

Optional Components and Features

The composition may also include other additives such as other antimicrobial agents, stabilizers, fragrances, dyes, pearlizing agents, vitamins and the like. Each additive, when present, may be added in amounts up to about 10% by weight, such as about 0.001 to about 10% by wt., or about 0.01 to about 5% by wt.

For example, in embodiments compositions may include additional components, which may in some instances further enhance antimicrobial activity. For example, compositions may include: alcohols such as methanol, ethanol, isopropanol, n-butanol, n-pentanol, benzyl alcohol and the like; mono- and poly-carboxylic acids such as acetic acid, glycolic acid, citric acid, salicylic acid and the like; and glycol ethers such as propylene glycol n-propyl ether, ethylene glycol n-propyl ether and the like. In some embodiments, a composition may not include additional components that enhance antimicrobial activity. For example, in embodiments, a composition may not include hydrogen peroxide.

In embodiments, the inorganic salt concentration of a composition may be maintained at a level that avoids substantial reactivity with the PAP. For example, in the case of a chloride-containing salt, such as sodium chloride, the PAP may react with the chloride ion which may lead to decomposition. Suitably, and as described herein, the salt concentration is not higher than about 0.2% by weight of a composition. One of skill in the art will be able to assess whether salt concentration is too high by assessing the odor level, a decrease in oxygen activity, and similar methods. One of skill in the art will also appreciate that combinations of formulation components can be selected in order to limit the inorganic salt concentration where appropriate.

The balance of the composition is typically water, or an aqueous medium (e.g., mixed solvent system, buffer, etc.) comprising water as the major component, so as to provide 100% by weight of a composition.

pH

The pH of compositions including PAP can affect both stability of the formulation and the antimicrobial activity. For example, lower pH may increase the antimicrobial activity, but may render the PAP insoluble. Higher pH may increase PAP solubility, but may reduce efficacy. In some embodiments, the compositions disclosed herein have a pH that is suitably selected to balance PAP solubility and efficacy. In embodiments the pH may be about 2.5 to about 4.5. Accordingly, the pH may be from about 3.0 to about 4.5, from about 4.0 to about 4.5, from about 3.0 to about 4.0, from about 3.5 to about 3.8, from about 3.6 to about 3.7, about 3.5, about 3.6, about 3.7 or about 3.8. In embodiments, a composition may have a pH of up to about 2.5, up to about 3.0, up to about 3.5, up to about 3.6, up to about 3.7, up to about 3.8, up to about 3.9, up to about 4.0, up to about 4.5, at least about 2.5, at least about 3.0, at least about 3.5, at least about 3.6, at least about 3.7, at least about 3.8, at least about 3.9, or at least about 4.0.

Composition pH can be adjusted with acid or base, if necessary. Any acid or base compatible with the components of the composition can be used. Exemplary acids include citric acid, phosphoric acid, gluconic acid, lactic acid, acetic acid, and glycolic acid. In some embodiments the acid is citric acid. Exemplary bases include sodium hydroxide, potassium hydroxide, and triethanolamine. Inorganic acids and bases may affect the inorganic salt content of the formulations, and may need to be monitored accordingly.

Viscosity

The composition may have a viscosity from about 100 to about 10000 centipoise, from about 500 to about 5000 centipoise, from about 1000 to about 2000 centipoise, or about 1000, about 1100, about 1200, about 1300, about 1400, about 1500, about 1600, about 1700, about 1800, about 1900 or about 2000 centipoise. For example, a composition may have a viscosity of at least about 100, at least about 200, at least about 300, at least about 400, at least about 500, at least about 600, at least about 700, at least about 800, at least about 900, at least about 1000, at least about 1100, at least about 1200, at least about 1300, at least about 1400, at least about 1500, at least about 2000, at least about 2300, at least about 3000, at least about 4000, at least about 5000, at least about 5500, at least about 6000, at least about 6500, at least about 7000, at least about 7500, at least about 8000, at least about 8500, at least about 9000, at least about 9500, at least about 10000, up to about 100, up to about 200, up to about 300, up to about 400, up to about 500, up to about 600, up to about 700, up to about 800, up to about 900, up to about 1000, up to about 1100, up to about 1200, up to about 1300, up to about 1400, up to about 1500, up to about 2000, up to about 2300, up to about 3000, up to about 4000, up to about 5000, up to about 5500, up to about 6000, up to about 6500, up to about 7000, up to about 7500, up to about 8000, up to about 8500, up to about 9000, up to about 9500, or up to about 10000 centipoise.

Viscosity can be determined, for example, using Brookfield RVT rotational viscometer. To achieve a suitable viscosity, a thickener may be present in the use composition in an amount from about 0.01 wt. % to about 5 wt. % of the total composition, from about 0.05 wt. % to about 2.5 wt. %, or from about 0.1 wt. % to about 1.5 wt. % of the total composition. Viscosity can be adjusted as desired or as required by the particular use, formulation, and/or delivery system associated with a particular composition, as will be understood by a person skilled in the art.

Methods of Making Compositions

The compositions may be generally prepared by any appropriate manufacturing processes and using any appropriate manufacturing equipment such as are known in the art. Suitably, the compositions can be prepared by dissolving the various components in water with stirring. Alternatively, components may be added to a commercially available product base, such as Soft Care Mild (Diversey, Sturtevant, Wis.). Such commercially available product bases may include components including but not limited to surfactants, humectants, thickening agents and the like, in an aqueous solution.

In embodiments, the compositions may be prepared at ambient temperature.

In an exemplary process, the various formulation components are sequentially added to water, with stirring between each addition to ensure dissolution and/or dispersion of the previous component. For example, a formulation may be prepared by first adding a thickening agent to water with stirring until the thickening agent fully disperses or dissolved. This may be followed by addition of one or more surfactants, followed by stirring to dissolve the surfactants fully. Additional components such as emollients, pearlizers, and the like can be added with stirring, and the pH can be adjusted followed by the addition of PAP. A final step may be further adjustment of the pH with base and/or acid, if necessary.

Equipment that can be used to prepare compositions described herein may be standard mixing devices. For example, a mixing vessel may include, but need not be limited to, a stainless steel vessel, such as S304 or SS316. The vessel may or may not be baffled. An agitator, such as, for example, a pitched blade turbine agitator may be used.

Methods of Use

Compositions described herein may be used as hand washes, for example, in the healthcare or patient care industries or in the food and beverage industry. The compositions may be efficacious against Gram-positive and Gram-negative bacteria, as well as viruses, fungi and yeasts.

The compositions may suitably be applied to the skin, optionally in the presence of water. For example, the skin may be first wetted with water, such as lukewarm tap water, followed by application of from about 0.5 mL to about 5 mL of the composition on to the skin. Using a normal hand washing routine wherein the complete hand is washed thoroughly, the composition may be contacted with the skin a period of time, for example, by rubbing the hands together. The contacting step may be carried out for contact times on the order of seconds to minutes. For example, the compositions may be applied to the skin for at least about 15 seconds, at least about 30 seconds, at least about 45 seconds, at least about 1 minute, at least about 2 minutes, at least about 3 minutes, at least about 4 minutes, at least about 5 minutes, up to about 15 seconds, up to about 30 seconds, up to about 45 seconds, up to about 1 minute, up to about 2 minutes, up to about 3 minutes, up to about 4 minutes, or up to about 5 minutes. The compositions may then be substantially removed from the skin, e.g., by rinsing with water. The hands can be dried, which may prevent skin irritation and cross-contamination.

Methods of Analysis

Compositions may be evaluated for antimicrobial activity using quantitative assays for bactericidal, virucidal or fungicidal activities and the like.

The "E2 antimicrobial" efficacy or standard refers to an antimicrobial kill property that is equivalent to or surpasses the efficacy of 50 ppm of available chlorine. The E2 standard is required by the United States Department of Agriculture for hand soaps used on site by employees in the meat and poultry processing industry, and has been adopted by restaurant establishments in the United States. A description of a test method used to determine whether a composition meets the E2 antimicrobial standard can be found in AOAC Official Method of Analysis No. 955.16, Official Methods of Analysis, 16th Ed. (1995), the entire contents of which are incorporated herein by reference.

Another test used to evaluate the antimicrobial properties of a composition is known as the time-kill test. In this test, the degree to which bacteria are killed when exposed to an antibacterial agent over time is recorded. In a time kill test, the test composition is diluted so that after addition of inoculum the test composition is at use concentration. The test composition is then brought into contact with a known population of test bacteria for a specified time period at a specified temperature. The antimicrobial ingredients are neutralized at the end of the time period and the sample is plated to enumerate the surviving bacteria. The percent reduction from the original population is then calculated.

Another test, the European standard EN 1276, is a quantitative suspension test for the evaluation of bactericidal activity of chemical disinfectants and antiseptics used in food, industrial, domestic and institutional areas. The test includes 4 obligatory bacterial test organisms: *Pseudomonas aeruginosa* ATCC 15442, *Escherichia coli* ATCC 10536, *Enterococcus hirae* ATCC 10541 and *Staphylococcus aureus* ATCC 6538. It also has obligatory bacterial concentrations between $1.5 \times 10^8$-$5 \times 10^8$ CFU/mL, and obligatory organic soil conditions, either clean conditions (0.3 g/L bovine serum albumin) or dirty conditions (3.0 g/L bovine serum albumin) Required contact times are 5 minutes and the required temperature is 20° C. Hard water must be used for making dilutions from concentrated products. A ≥5 Log Reduction must be achieved for the product in question to be considered passing for this standard under the conditions listed above.

Additionally, the European standard EN 13727 is a quantitative suspension test for the evaluation of bactericidal activity in the medical area for instruments/surfaces and hygienic hand washes and handrubs. The test includes 3 obligatory bacterial test organisms: *Pseudomonas aeruginosa* ATCC 15442, *Enterococcus hirae* ATCC 10541 and *Staphylococcus aureus* ATCC 6538. It also has obligatory bacterial concentrations between $1.5 \times 10^8$-$5 \times 10^8$ CFU/mL, and obligatory organic soil conditions, either clean conditions (0.3 g/L bovine serum albumin) or dirty conditions (3.0 g/L bovine serum albumin+3 mL/L sheep erythrocytes). Required contact times are 1 minute for hand wash products and 5 minutes for surgical hand wash products. The obligatory test temperature is 20° C., and hard water must be used for making dilutions from concentrated products. A ≥3 Log Reduction must be achieved for the hand wash products in question to be considered passing for this standard under the conditions listed above.

Another test is the European standard EN 1650, which is an evaluation of fungicidal and yeasticidal efficacy. A ≥4 Log Reduction must be achieved for the compositions in question to be considered passing for this standard.

The formulation activity may be assessed at various time points to determine overall stability and effectiveness. For example, a composition described herein may have antimicrobial activity for at least about 16 months. For example, a composition may be subjected to testing under any of the above European standards following storage at a particular temperature for a period of time. In embodiments, a composition described herein may have a ≥3 log reduction, ≥4 Log Reduction, or ≥5 Log Reduction in a European standard such as EN 1276, EN 13727, or EN 1650 under the obligatory test conditions for the indicated test, following storage for at least about 1 month, at least about 2 months, at least about 3 months, at least about 4 months, at least about 5 months, at least about 6 months, at least about 7 months, at least about 8 months, at least about 9 months, at least about 10 months, at least about 11 months, at least about 12 months, at least about 13 months, at least about 14 months, at least about 15 months, or at least about 16 months.

Compositions can also be assayed to determine active oxygen content over time.

The following non-limiting Examples are intended to be purely illustrative, and show specific experiments that were carried out in accordance with the disclosure.

EXAMPLES

Example 1

Exemplary Formulations

Four exemplary formulations are illustrated in Table 3. PAP was purchased from Chemicals as EURECO™ HC L17, and used as received. All other components were purchased from commercial suppliers and used as received. Water used to make the formulations was deionized and chlorinated. All values are weight percentages of the components as supplied.

TABLE 3

Exemplary formulations

| | Formulation | | | |
|---|---|---|---|---|
| | 1 | 2 | 3 | 4 |
| Water | 69.92 | 69.92 | 73.80 | 75.95 |
| PAP (17%) | 4.00 | 4.00 | 4.00 | 2.50 |
| Sodium lauryl ether sulfate (12-14), 1 EO (70%) | 14.00 | — | — | — |
| Sodium lauryl ether sulfate (12-14), 2 EO (70%) | — | 14.00 | 5.00 | 8.00 |
| Fatty (coco) acid diethanolamide (80%) | 1.00 | 1.00 | — | — |
| Sodium dodecyl sulfate (97%) | — | — | 7.00 | 4.00 |
| Hydroxyethyl cellulose (100%) | — | — | 1.00 | 1.25 |
| Polyacrylic acid (MW = 4000 kDa) (100%) | 0.40 | 0.40 | — | — |
| Isopropyl myristate (100%) | 0.20 | 0.20 | 0.40 | 0.50 |
| Glycerol (99%) | 5.00 | 5.00 | 5.00 | 5.50 |
| Pearlizer concentrate (Glycoldistearate, glycerin, laureth-4, cocamidopropyl beatine) (60%) | 3.00 | 3.00 | 3.00 | 1.50 |
| Citric acid (91%) | 0.98 | 0.98 | 0.70 | 0.70 |
| Sodium chloride (100%) | 1.50 | 1.50 | — | — |
| Sodium hydroxide (50%) | — | — | 0.10 | 0.10 |

For each of formulations 1-4, the final pH was 3.6, and viscosity was 1300 mPas.

Formulation 3 was prepared as follows. To water was added hydroxyethyl cellulose, and the mixture was stirred until the hydroxyethyl cellulose fully dispersed in to the water. The surfactants were then added with stirring until they fully dissolved. The NaOH was added to swell the hydroxyethyl cellulose, followed by pH adjustment with citric acid. Glycerol and isopropyl myristate were added next with stirring until they fully dissolved. The pearlizer concentrate and the PAP were then added with stirring. Other formulations were prepared in an analogous manner.

Example 2

Antimicrobial Activities of Compositions

Figure 1:
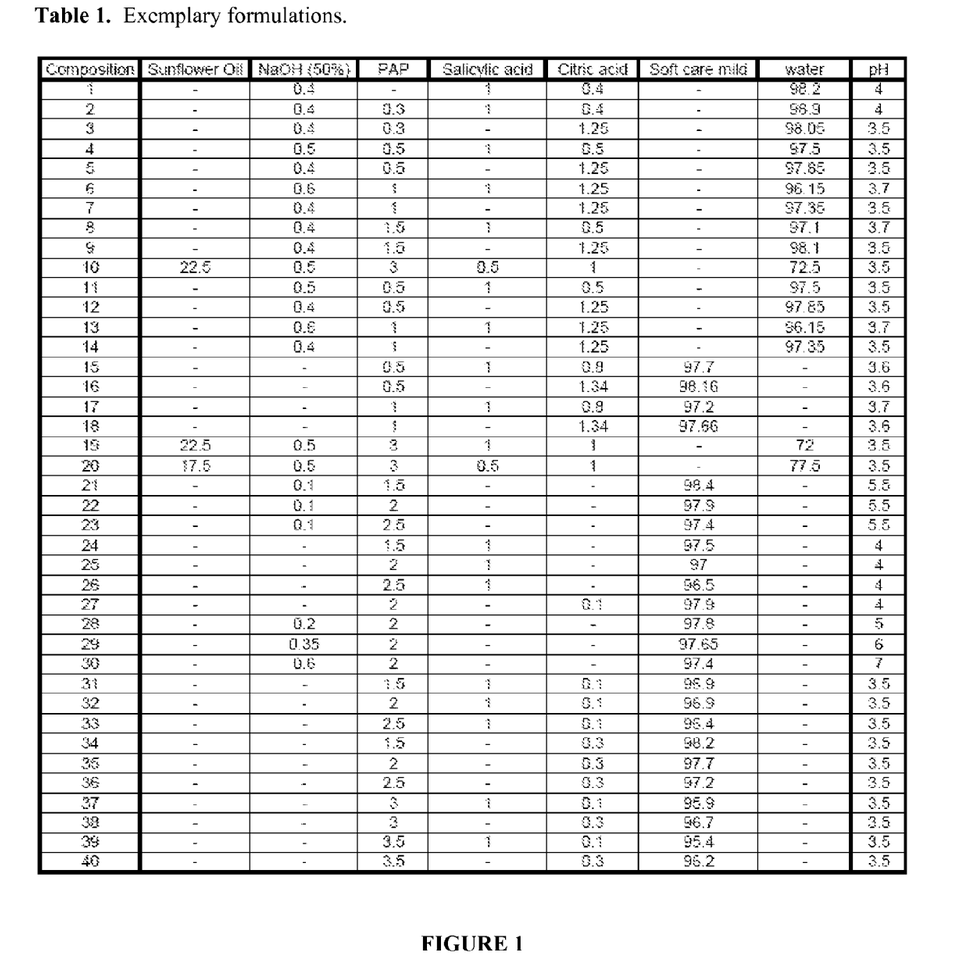
FIG. 1 depicts a table (Table 1) of exemplary formulations.

Additional exemplary formulations including PAP and various other components were prepared and subjected to testing under European standard EN 13727, to determine antimicrobial activity against *Pseudomonas aeruginosa* ATCC 15442 and *Staphylococcus aureus* ATCC 6538. Both clean conditions (0.3 g/L bovine serum albumin) and dirty conditions (3.0 g/L bovine serum albumin+3 mL/L sheep erythrocytes) were tested. Formulations optionally included sodium hydroxide and/or citric acid for pH adjustment, salicylic acid as an optional additional antimicrobial agent, sunflower oil as an emollient, and the product base Soft Care Mild, which is commercially available from Diversey (Sturtevant, Wis., now part of Sealed Air). The formulations are described in FIG. 1, Table 1.

Results are illustrated in FIG. 2, Table 2, where the values represent the log reduction in bacteria. When the product base is present, full kill at 30 second contact times is observed, with or without salicylic acid, at 3 wt % or 3.5 wt % PAP at a pH of 3.5.

Example 3

Formulation Activity Over Time

The activity of formulation 3 described above was determined by measuring the activity of PAP over time at two different temperatures. The activity of PAP was measured by titrating to determine the active oxygen content. Results are illustrated in Table 4, where the time T indicates the number of weeks from the start time. Table entries with the entry "-" indicate that the data was not measured under the indicated conditions.

TABLE 4

Stability data

| Time | 5° C. | 20° C. | 40° C. |
|---|---|---|---|
| T = 0 | — | 0.69% | |
| T = 2 | — | 0.55% | 0.52% |
| T = 4 | — | 0.54% | 0.39% |
| T = 6 | — | 0.23% | 0.17% |
| T = 8 | — | 0.39% | 0.24% |
| T = 12 | — | 0.27% | 0.22% |
| 4 months | — | 0.33% | 0.29% |
| 5 months | — | 0.38% | 0.21% |
| 6 months | — | 0.36% | 0.16% |
| 7 months | — | 0.36% | 0.12% |
| 8 months | — | 0.25% | 0.14% |
| 9 months | — | 0.35% | 0.22% |
| 10 months | — | 0.30% | 0.19% |
| 11 months | — | 0.32% | 0.15% |
| 12 months | 0.43% | 0.16% | 0.11% |
| 16 months | — | 0.20% | 0.07% |

Example 4

Antimicrobial Activities of Compositions

Formulation 3 described above was subjected to testing under European standard EN 1276, to determine antimicrobial activity against *Pseudomonas aeruginosa* ATCC 15442, *Staphylococcus aureus* ATCC 6538, *Escherichia coli* ATCC 10536 and *Enterococcus hirae* ATCC 10541. Results are illustrated in Tables 5-8, where the values represent the log reduction in bacteria. Contact times were 30 seconds. Table entries with the entry "-" indicate that the data was not measured under the indicated conditions.

TABLE 5

Antimicrobial testing data

| | *P. aeruginosa* ATCC 15442 | | | | | |
|---|---|---|---|---|---|---|
| | Clean conditions | | | Dirty conditions | | |
| | 80% | 50% | 25% | 80% | 50% | 25% |
| Day 14 Ambient | >5.32 | >5.32 | >5.32 | — | — | — |
| Day 57 Ambient | — | — | — | >5.02 | >5.02 | >5.02 |
| 16 months Ambient | >6.70 | — | — | >6.70 | — | — |
| Day 52 at 40 C. | >5.29 | >5.29 | >5.29 | — | — | — |
| 7 months at 40 C. | >6.58 | >6.58 | >6.58 | >6.58 | >6.58 | >6.58 |
| 16 months at 40 C. | — | — | — | >6.70 | — | — |

TABLE 6

Antimicrobial testing data

E. coli ATCC 10536

| | Clean conditions | | | Dirty conditions | | |
|---|---|---|---|---|---|---|
| | 80% | 50% | 25% | 80% | 50% | 25% |
| Day 14 Ambient | >5.35 | >5.35 | >5.35 | — | — | — |
| Day 57 Ambient | — | — | — | >5.3 | >5.3 | >5.3 |
| 16 months Ambient | >6.70 | — | — | >6.70 | — | — |
| Day 52 at 40 C. | >5.32 | >5.32 | >5.32 | — | — | — |
| 7 months at 40 C. | >6.45 | >6.45 | >6.45 | >6.45 | >6.45 | >6.45 |
| 16 months at 40 C. | — | — | — | >6.70 | — | — |

TABLE 7

Antimicrobial testing data

S. aureus ATCC 6538

| | Clean conditions | | | Dirty conditions | | |
|---|---|---|---|---|---|---|
| | 80% | 50% | 25% | 80% | 50% | 25% |
| Day 14 Ambient | >5.06 | >5.06 | >5.06 | — | — | — |
| Day 57 Ambient | — | — | — | >5.09 | >5.09 | >5.09 |
| 16 months Ambient | >6.50 | — | — | >6.50 | — | — |
| Day 52 at 40 C. | >5.19 | >5.19 | >5.19 | — | — | — |
| 7 months at 40 C. | >6.36 | >6.36 | >6.36 | >6.36 | >6.36 | >6.36 |
| 16 months at 40 C. | — | — | — | >6.50 | — | — |

TABLE 8

Antimicrobial testing data

E. hirae ATCC 10541

| | Clean conditions | | | Dirty conditions | | |
|---|---|---|---|---|---|---|
| | 80% | 50% | 25% | 80% | 50% | 25% |
| Day 14 Ambient | >5.26 | >5.26 | >5.26 | — | — | — |
| Day 57 Ambient | — | — | — | >5.23 | >5.23 | >5.23 |
| 16 months Ambient | >6.70 | — | — | >6.70 | — | — |
| Day 52 at 40 C. | >5.27 | >5.27 | >5.27 | — | — | — |
| 7 months at 40 C. | >6.50 | >6.50 | >6.50 | >6.50 | >6.50 | >6.50 |
| 16 months at 40 C. | — | — | — | >6.70 | — | — |

All patents, publications and references cited herein are hereby fully incorporated by reference. In case of conflict between the present disclosure and incorporated patents, publications and references, the present disclosure should control.

What is claimed is:

1. A hand wash composition comprising:
   from about 0.3 wt % to about 8.0 wt % phthalimido-peroxy-hexanoic acid;
   at least one anionic surfactant; and
   at least one emollient;
   wherein the composition has a maximum inorganic salt concentration of 0.2 wt %, and pH of from about 2.5 to about 4.5.

2. The composition of claim 1, wherein at least one anionic surfactant is selected from the group consisting of alkyl sulfates and alkyl ether sulfates.

3. The composition of claim 2, wherein at least one anionic surfactant is selected from the group consisting of sodium lauryl ether sulfate and sodium lauryl sulfate.

4. The composition of claim 1, wherein at least one anionic surfactant is present in an amount of about 1-15% by weight.

5. The composition of claim 1, further comprising at least one thickening agent.

6. The composition of claim 5, wherein at least one thickening agent is selected from the group consisting of acrylic acid polymers, cellulose, modified celluloses, xanthan gums, and magnesium sulfate.

7. The composition of claim 5, wherein at least one thickening agent is present in an amount of about 0.05-5% by weight.

8. The composition of claim 1, wherein at least one emollient is selected from the group consisting of propylene glycol, glycerol, isopropyl myristate and isopropyl palmitate.

9. The composition of claim 1, wherein at least one emollient is present in an amount of about 0.01-2% by weight.

10. The composition of claim 1, further comprising at least one component selected from the group consisting of stabilizers, humectants, pearlizers, fragrances and dyes.

11. The composition of claim 1, wherein the composition has an effective amount of antimicrobial activity for at least about 16 months.

12. A method of disinfecting the skin, comprising contacting the skin with a composition comprising:
    from about 0.3 wt % to about 8.0 wt % phthalimido-peroxy-hexanoic acid; and
    at least one emollient, wherein the composition has a pH of from about 2.5 to about 4.5.

13. The method of claim 12, wherein the composition further comprises at least one surfactant, or at least one thickening agent.

14. The method of claim 13, wherein at least one surfactant is an anionic surfactant, or wherein at least one thickening agent is selected from the group consisting of acrylic acid polymers, cellulose, modified celluloses, xanthan gums, and magnesium sulfate.

15. The method of claim 13, wherein at least one anionic surfactant is present in an amount of about 1-15% by weight.

16. The method of claim 12, wherein the composition has a maximum inorganic salt concentration of 0.2 wt %.

17. The method of claim 13, wherein at least one thickening agent is present in an amount of about 0.05-5% by weight.

18. The method of claim 12, wherein at least one emollient is present in an amount of about 0.01-2% by weight.

19. The method of claim 12, wherein the composition further comprises at least one component selected from the group consisting of stabilizers, humectants, pearlizers, fragrances and dyes.

20. The method of claim 12, wherein the composition has antimicrobial activity for at least up to 16 months.

21. The method of claim 12, comprising contacting the skin with the composition for a contact time of 15 seconds.

22. The method of claim 12, wherein contacting the skin with the composition for 30 seconds results in at least a 3-log reduction in microorganisms selected from bacteria, yeasts, fungi and viruses.

23. The method of claim 12 further comprising rinsing the skin with water after the contacting step.

24. The method of claim 12, wherein at least one emollient is selected from the group consisting of propylene glycol, glycerol, isopropyl myristate and isopropyl palmitate.

25. The method of claim 14, wherein at least one anionic surfactant is selected from the group consisting of alkyl sulfates and alkyl ether sulfates.

26. The method of claim 25, wherein at least one anionic surfactant is selected from the group consisting of sodium lauryl ether sulfate and sodium lauryl sulfate.

* * * * *